United States Patent
Alniami

(10) Patent No.: US 12,083,233 B1
(45) Date of Patent: Sep. 10, 2024

(54) SANITIZING STATION AND METAL DETECTION SYSTEM

(71) Applicant: Laith Ismail Alniami, Palmdale, CA (US)

(72) Inventor: Laith Ismail Alniami, Palmdale, CA (US)

( * ) Notice: Subject to any disclaimer, the term of this patent is extended or adjusted under 35 U.S.C. 154(b) by 0 days.

(21) Appl. No.: 18/127,602

(22) Filed: Mar. 28, 2023

Related U.S. Application Data

(63) Continuation-in-part of application No. 17/706,415, filed on Mar. 28, 2022, now Pat. No. 11,551,503.

(51) Int. Cl.
| | |
|---|---|
| *A61L 2/00* | (2006.01) |
| *A61G 10/00* | (2006.01) |
| *A61L 2/26* | (2006.01) |
| *A61L 9/16* | (2006.01) |

(52) U.S. Cl.
CPC .......... *A61L 2/0047* (2013.01); *A61G 10/005* (2013.01); *A61L 2/26* (2013.01); *A61L 9/16* (2013.01); *A61L 2202/11* (2013.01); *A61L 2209/16* (2013.01)

(58) Field of Classification Search
CPC . A61L 2/0047; A61L 2/26; A61L 9/16; A61L 2202/11; A61L 2209/16; A61G 10/005
See application file for complete search history.

(56) References Cited

U.S. PATENT DOCUMENTS

| | | | |
|---|---|---|---|
| 11,904,066 B2 * | 2/2024 | Rosenblat | .................. A61L 2/26 |
| 2012/0228812 A1 | 9/2012 | Oosawa | |
| 2017/0124813 A1 | 5/2017 | Misener | |
| 2018/0005206 A1 | 1/2018 | Belin et al. | |
| 2021/0330832 A1 | 10/2021 | Dobbins et al. | |
| 2022/0031897 A1* | 2/2022 | Saxena | ...................... A61L 2/26 |
| 2022/0241451 A1* | 8/2022 | Johnston | .................... F24F 8/22 |

(Continued)

FOREIGN PATENT DOCUMENTS

| | | | | |
|---|---|---|---|---|
| CA | 3096669 A1 * | 10/2019 | ............ | A23L 3/001 |
| CN | 213826093 U | 7/2021 | | |
| CN | 214276052 U * | 9/2021 | | |

(Continued)

OTHER PUBLICATIONS

Cn 115581578A—Fast negative pressure ventilation isolation system for respiratory infectious disease control, 9 pages. (Year: 2024).*

(Continued)

*Primary Examiner* — Tuyen K Vo
(74) *Attorney, Agent, or Firm* — Plager Schack LLP; Mark H. Plager; Michael J. O'Brien

(57) ABSTRACT

A sanitizing station system is configured to deactivate microbes. The sanitizing station system has a housing is joined to a testing desk; the housing further comprises pressurized hot air system, and ultraviolet light system. A ventilation system is arranged proximate the housing and joined to the housing with ducting. A vacuum system is arranged in the housing and further has drain vacuum tracks connected to a plurality of vacuums divided from one another with a divider proximate a heater cable. A vertical ventilation passthrough arranged proximate the drain vacuum tracks. The pressurized hot air system is operatively coupled to a heat control speed switch.

4 Claims, 3 Drawing Sheets

(56) References Cited

U.S. PATENT DOCUMENTS

2022/0361717 A1* 11/2022 Braxton ............... A47K 5/1202
2024/0058193 A1* 2/2024 Ta ........................ A61G 10/023

FOREIGN PATENT DOCUMENTS

CN    115581578 A  *  1/2023   ......... B01D 46/0028
EP      3932435 A1  *  1/2022   ........... A61L 2/0047

OTHER PUBLICATIONS

CN214276052U—Sterilizing and anti-virus ventilator, 5 pages. (Year: 2024).*

International Search Report and Written Opinion issued on Aug. 17, 2023 in corresponding International Application No. PCT/US2023/023449; 7 pages.

* cited by examiner

SANITIZING STATION AND METAL DETECTION SYSTEM

RELATED APPLICATION

This application is a continuation-in-part of non-provisional patent application U.S. Ser. No. 17/706,415 filed on Mar. 28, 2022, the entire contents of which is herein incorporated by reference.

BACKGROUND

The embodiments herein relate generally to devices that deactivate microbiomes.

Prior to embodiments of the disclosed invention, there was no device that sanitized humans from COVID-19. Embodiments of the disclosed invention solve these problems.

SUMMARY

A sanitizing station system is configured to deactivate microbes. The sanitizing station system has a housing is joined to a testing desk; the housing further comprises pressurized hot air system, and ultraviolet light system. All users must wear a goggles to protect their eyes from the x-rays of ultraviolet light system. A ventilation system is arranged proximate the housing and joined to the housing with ducting. A vacuum system is arranged in the housing and further has drain vacuum tracks connected to a plurality of vacuums divided from one another with a divider proximate a heater cable. A vertical ventilation passthrough arranged proximate the drain vacuum tracks. The pressurized hot air system is operatively coupled to a heat control speed switch.

BRIEF DESCRIPTION OF THE FIGURES

The detailed description of some embodiments of the invention is made below with reference to the accompanying figures, wherein like numerals represent corresponding parts of the figures.

DETAILED DESCRIPTION OF CERTAIN EMBODIMENTS

Figure 1:
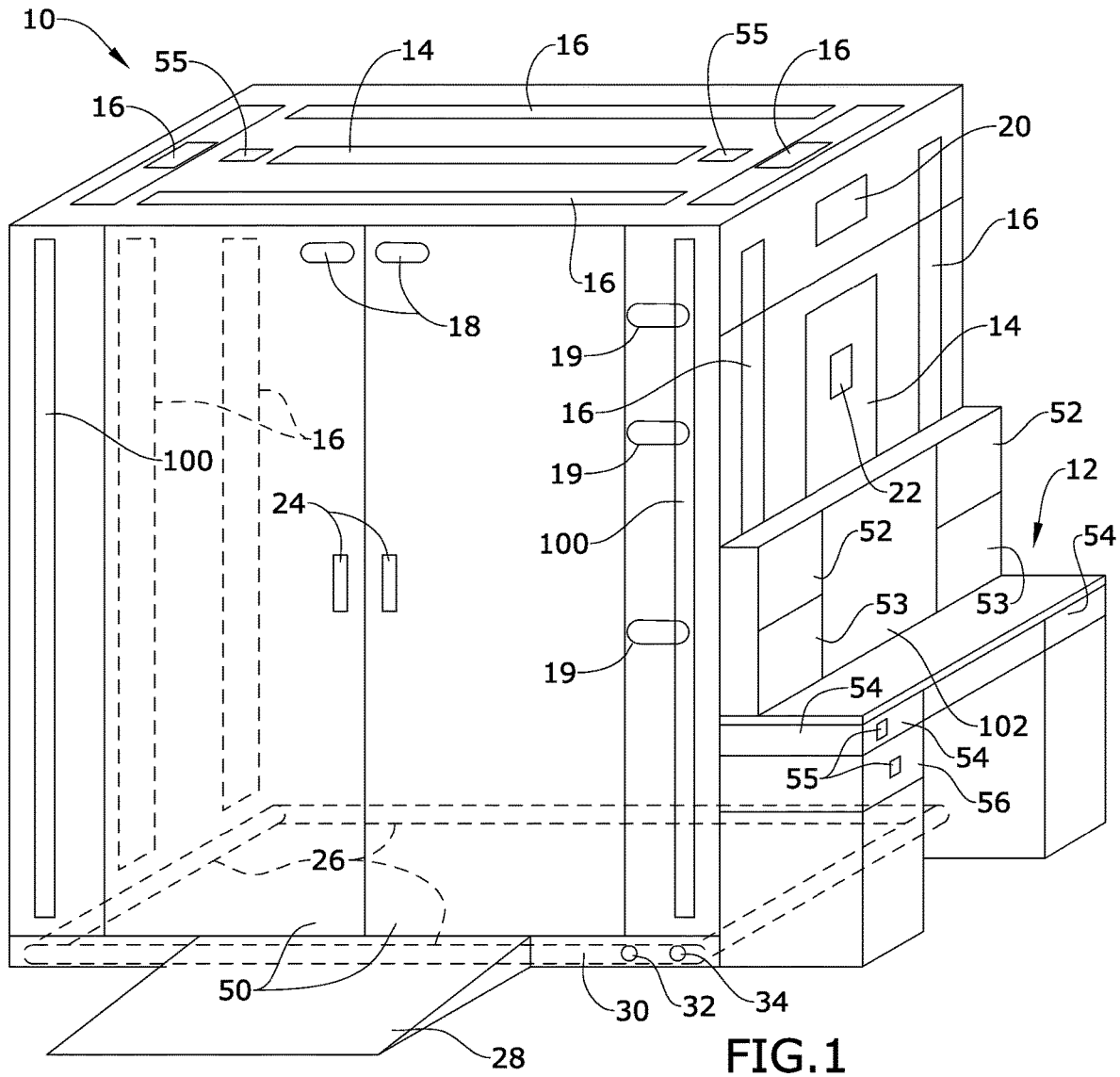
FIG. 1 shows a perspective view of one embodiment of the present invention.
Figure 2:
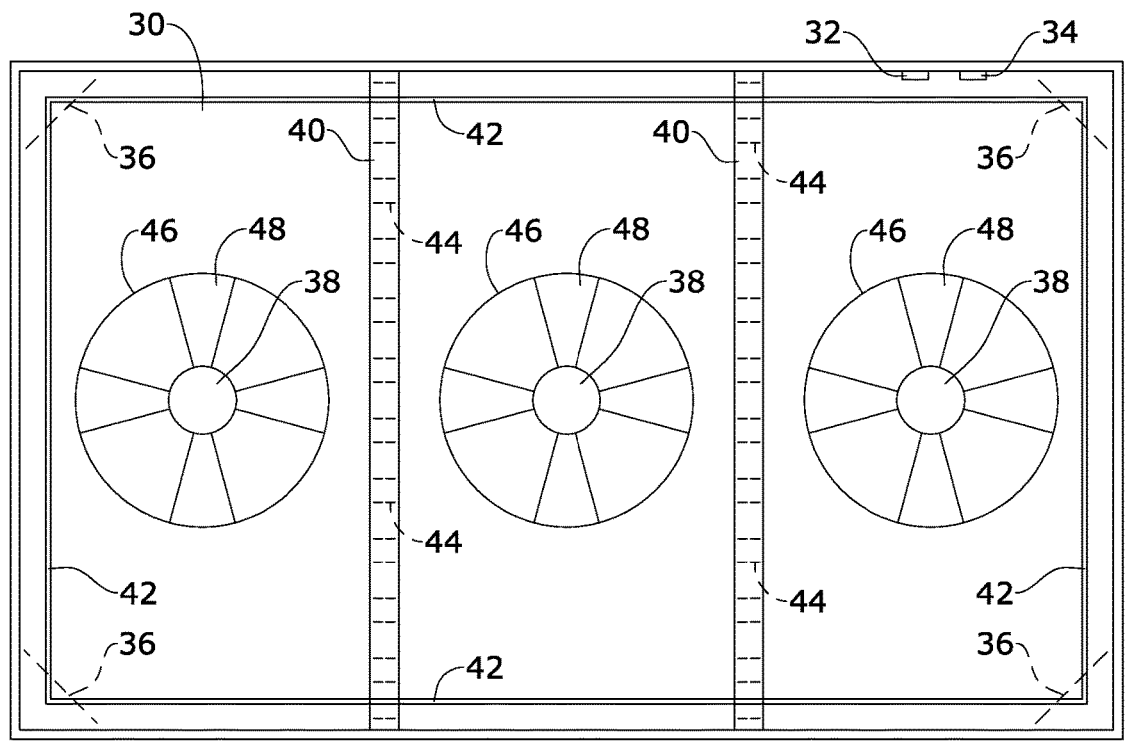
FIG. 2 shows a bottom view of one embodiment of the present invention.

By way of example, and referring to FIG. 1, one embodiment of a sanitizing station system 10 further comprises a housing. The housing is joined to a testing desk 12. The housing further comprises pressurized hot air system 14, and ultraviolet light system 16. The housing may be accessed through doors 50 further comprising motion detectors 18, handles 24, and metal detectors 100. A ramp 28 can be used to assist users with mobility issues.

An air purifier is 0.03 micron filter back to back to carbonated filter an air purifier control switch 20. The pressurized hot air system 14 is operatively coupled to a heat control speed switch 22. A ventilation system is arranged proximate the housing and joined to the housing with ducting. The ventilation system further comprises the air purifier.

A vacuum system to heat and sanitize the air going out further comprises drain vacuum tracks 26 connected to a vacuum 30. The vacuuming system further comprises a vertical ventilation passthrough 36 arranged proximate the drain vacuum tracks 26. The vacuum system uses more than one vacuum 30 divided from at least one other vacuum 30 with a divider 40 proximate a heater cable 42. Each vacuum further comprises a fan motor 38 joined to a fan 46 having fan blades 48.

A computer 102 digitalizes data and send it to mainframe, and to report collected data to Center of Disease Control help center. The testing desk 12 further comprises first cabinets 52, second cabinets 53, drawer money sanitizer for small items 54, and a sanitizer drawer for big items 56. A digital camera 55 with a sim card is fixed to the testing desk 12. A computer 102 is arranged on the testing desk 12.

Figure 3:
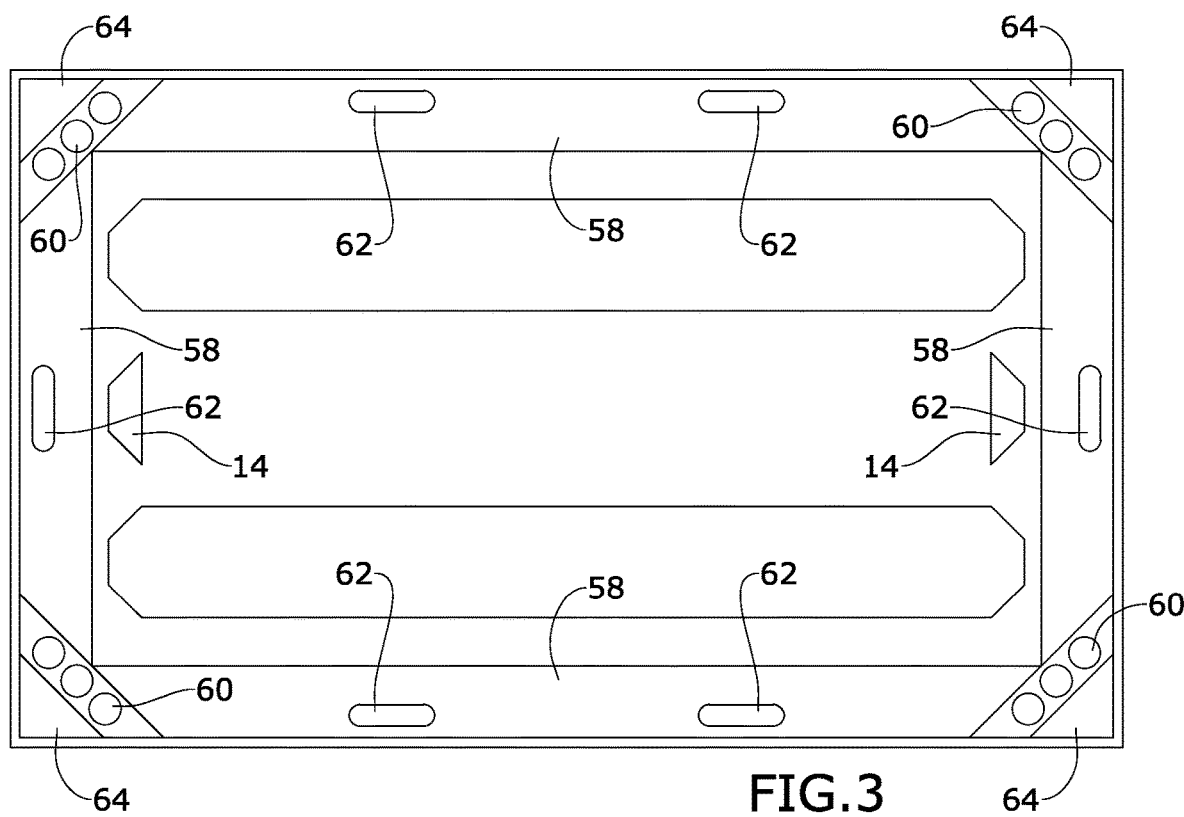
FIG. 3 shows a top view of one embodiment of the present invention.

FIG. 3 shows the pressurized hot air system 14 in more detail. Hot air pressure system 14 further comprises: at least one horizontal ultraviolet light 58, at least one vertical ultraviolet light 60, at least one motion light 62, and a ventilation system 64 for the vacuuming system.

Figure 4:
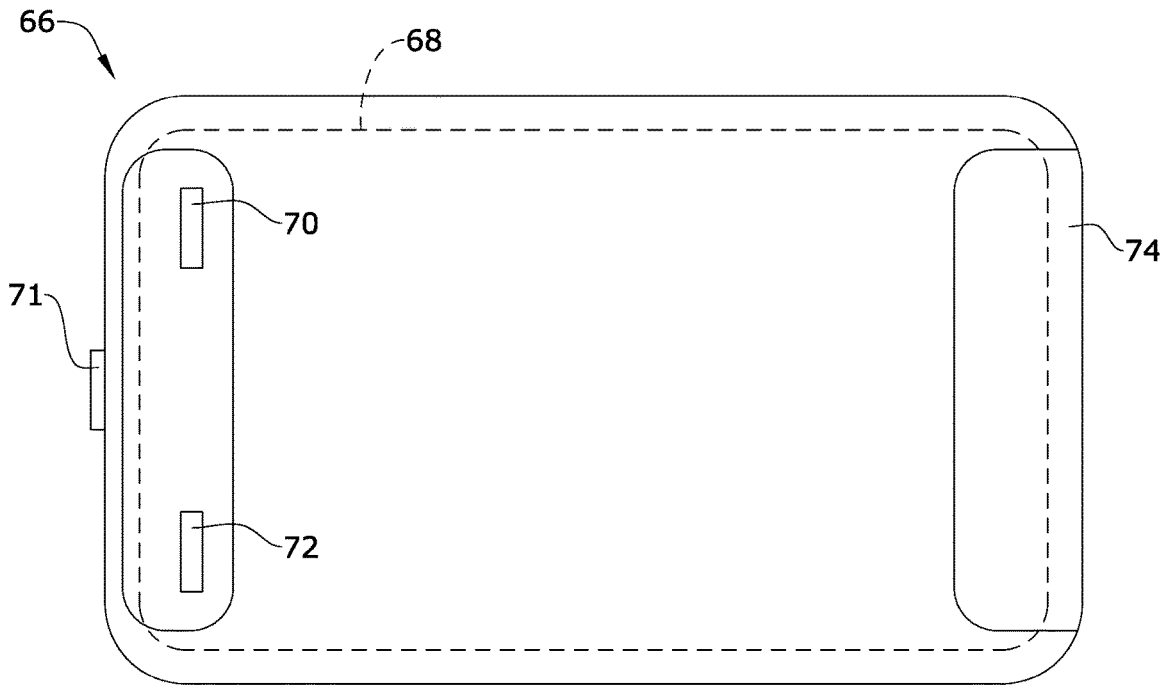
FIG. 4 shows a top view of one embodiment of the present invention.
Figure 5:
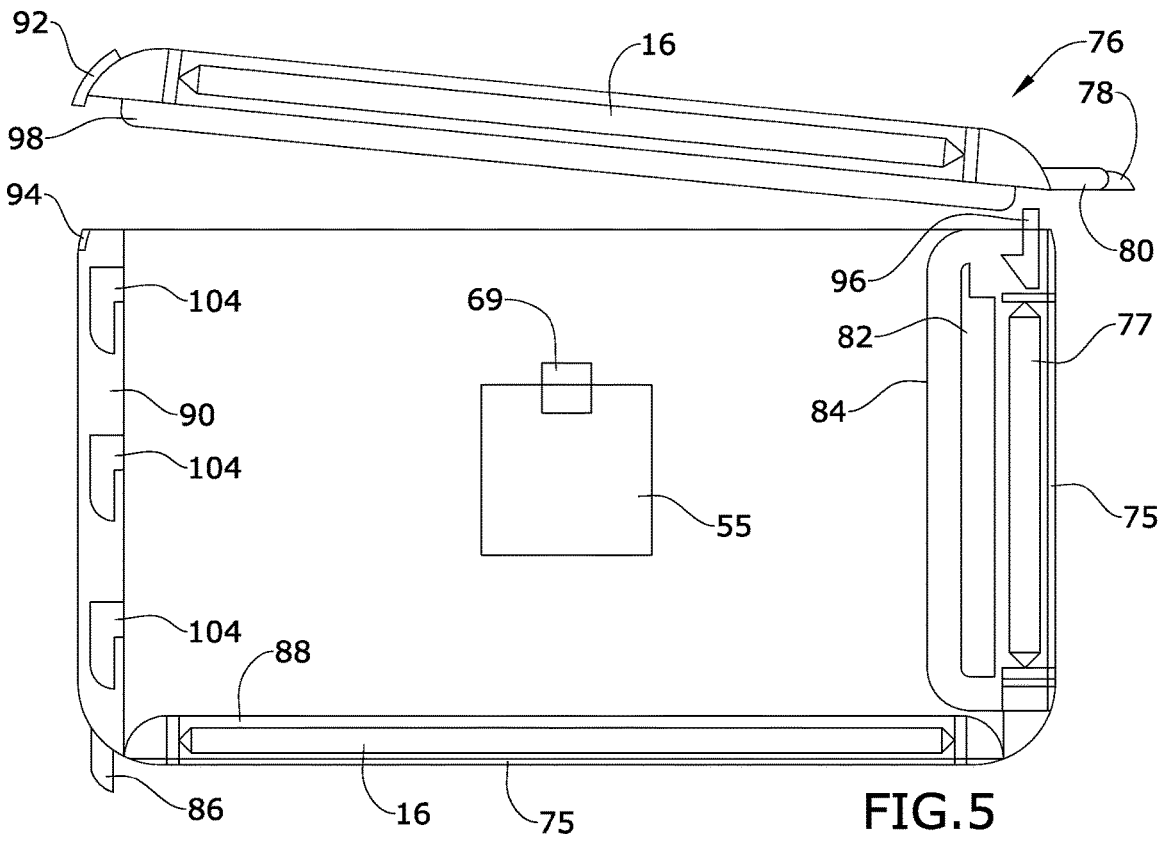
FIG. 5 shows a left and a right side view of one embodiment of the present invention.

FIG. 4 shows a sanitizing station 66 which can be located in either or both of the drawer money sanitizer for small items 54, and the sanitizer drawer for big items 56. The sanitizing station 66 further comprises at least on ultraviolet screen 84, 88 and 98, a time controller 70, a heat controller 72, and a fan blower 74 electrically coupled to a microcontroller. The sanitizing station 66 further comprises a housing joined to a handle 71.

A clothing and backpack cleaner 76 further comprises a hot air supply connection 78 joined to an electrical power supply 80. The electrical power supply 80 is electrically coupled to an ultraviolet light system 16. The hot air supply connection 78 is joined to at least one hot air dispenser 104. A first ultraviolet light system 16 and a second ultraviolet light system 98 are joined to a clothing and backpack sanitizer latch 92. The clothing and backpack sanitizer latch 92 can be mechanically coupled to clothing and backpack sanitizer latch 94. The electrical power supply 80 is further electrically coupled to a power connection 96.

As used in this application, the term "a" or "an" means "at least one" or "one or more."

As used in this application, the term "about" or "approximately" refers to a range of values within plus or minus 10% of the specified number.

As used in this application, the term "substantially" means that the actual value is within about 10% of the actual desired value, particularly within about 5% of the actual desired value and especially within about 1% of the actual desired value of any variable, element or limit set forth herein.

All references throughout this application, for example patent documents including issued or granted patents or equivalents, patent application publications, and non-patent literature documents or other source material, are hereby incorporated by reference herein in their entireties, as though individually incorporated by reference, to the extent each reference is at least partially not inconsistent with the disclosure in the present application (for example, a reference that is partially inconsistent is incorporated by reference except for the partially inconsistent portion of the reference).

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Any element in a claim that does not explicitly state "means for" performing a specified function, or "step for" performing a specified function, is not to be interpreted as a "means" or "step" clause as specified in 35 U.S.C. § 112, 16. In particular, any use of "step of" in the claims is not intended to invoke the provision of 35 U.S.C. § 112, 16.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A sanitizing station system, is configured to deactivate microbes; the sanitizing station system comprising:
   a housing is joined to a testing desk; the housing further comprises a pressurized hot air system, and ultraviolet light system;
   a ventilation system is arranged proximate the housing and joined to the housing with ducting;
   a vacuum system, is arranged in the housing and further comprises:
   drain vacuum tracks connected to a plurality of vacuums divided from one another with a divider proximate a heater cable;
   a vertical ventilation passthrough arranged proximate the drain vacuum tracks;
   the pressurized hot air system is operatively coupled to a heat control speed switch.

2. The sanitizing system of claim 1, wherein the housing further comprises doors further comprising motion detectors, handles, and metal detectors; and a ramp wherein the ramp is used to assist users with mobility issues.

3. The sanitizing system of claim 2, wherein the ventilation system further comprises an air purifier and the air purifier is operationally connected to an air purifier control switch.

4. The sanitizing system of claim 3, wherein each of the plurality of vacuums further comprises a fan motor joined to a fan having fan blades.

* * * * *